United States Patent [19]

Hodgson

[11] Patent Number: 4,501,673
[45] Date of Patent: Feb. 26, 1985

[54] COMPOSITIONS FOR USE IN OIL RECOVERY AND METHOD OF USE

[75] Inventor: Phillip K. G. Hodgson, Reading, England

[73] Assignee: The British Petroleum Company p.l.c., London, England

[21] Appl. No.: 363,864

[22] Filed: Mar. 31, 1982

[30] Foreign Application Priority Data

Apr. 3, 1981 [GB] United Kingdom ............... 8110559

[51] Int. Cl.$^3$ ............................................ E21B 43/22
[52] U.S. Cl. ............................. 252/8.55 D; 166/274; 546/294; 546/318; 546/326
[58] Field of Search ................. 252/8.55 D; 166/274, 166/275; 260/501.13, 501.12; 546/294, 296, 298, 301, 318, 326

[56] References Cited

U.S. PATENT DOCUMENTS 4,216,297  8/1980  Stournas .................. 252/8.55 D

OTHER PUBLICATIONS

*J. Med. Chem.*, 1967, 10, 158-161.

Primary Examiner—Herbert B. Guynn
Attorney, Agent, or Firm—Morgan, Finnegan, Pine, Foley & Lee

[57] ABSTRACT

Betaines containing the pyridine nucleus, some of which are novel per se, are dissolved in sea water or formation water, the concentration of betaine being from 200 to 100,000 ppm, to give a surfactant solution suitable for displacing crude oil from a formation in an enhanced oil recovery process. These betaines have low interfacial tension (against oil), a high tolerance towards divalent metal ions and good temperature stability as compared with betaines previously proposed for enhanced oil recovery.

3 Claims, No Drawings

COMPOSITIONS FOR USE IN OIL RECOVERY AND METHOD OF USE

This invention relates to surfactant compositions suitable for injection into an oil bearing formation, more particularly to low concentration surfactant compositions containing betaines and to a method of using same in the recovery of crude oil.

The displacement of oil in a formation by the use of betaine surfactants has been previously published in, for example, U.K. Pat. No. 1516284 and U.S. Pat. No. 3,939,911, 4,193,452 and 4,216,097.

It has now been found that a class of betaines derived from pyridine are particularly effective for the displacement of crude oil and superior in certain respects to betaines which have been previously described for this purpose.

According to the present invention an aqueous surfactant composition suitable for injection into an oil bearing formation to assist in the recovery of the oil comprises an aqueous medium which has dispersed therein a betaine of formula:

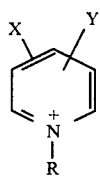
(A)

where
- R is $C_8$ to $C_{24}$ alkyl which may optionally be substituted by inert substituents;
- X is $CO_2^-$ or $SO_3^-$ or X is $(CH_2)_m SO_3^-$ where m is 1 or 2 when Y is H;
- or X is $CO_2^-$ when Y is $CO_2^-$;
- or X is $SO_3^-$ when Y is $SO_3^-$.

When R is $C_{16}$ or higher the compounds are novel per se.

Thus according to one aspect of the invention there are provided new compounds of formula A where R is $C_{16}$ to $C_{24}$ alkyl.

The surfactant of formula (A) is suitable for use where the water in which it is to be dispersed contains a high concentration of cations and anions as, for example, sea water from the North Sea or formation water with a total ionic content up to 150,000 ppm including 50,000 ppm divalent ions.

The surfactant composition is usually suitable for use at low concentrations of betaine of formula (A), for example, as low as 200 ppm. There is no upper limit but a concentration of 100,000 ppm will not usually be exceeded.

The surfactant composition can be employed in an enhanced oil recovery operation in which the surfactant composition is injected and then followed by a drive fluid such as water. It may also be used to increase the injectivity of water injection wells.

Compounds of formula:

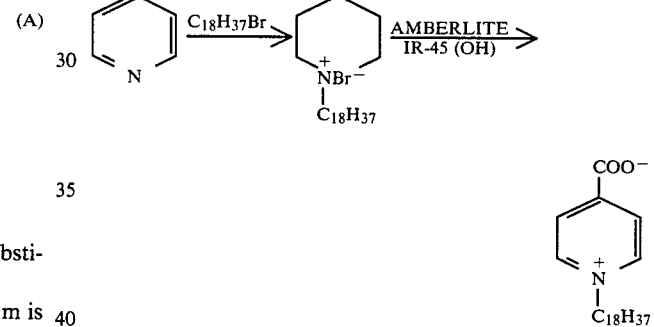

have been previously described in *J. Med. Chem.*, 1967, 10, 158 and were stated to have use as cholesterol-solubilising agents.

The invention is illustrated by the following Examples.

EXAMPLE 1

Preparation of 1-octadecylpyridinium-4-carboxylate

Isonicotinic acid (30.75 g, 0.25M) and 1-bromooctadecane (116 g, 0.35M) were heated to 220° with efficient mechanical stirring. The mixture was allowed to cool to 190° over 0.5 h and then to 100°. Ethanol (200 ml) was added and the mixture was digested at 100°. Unused isonicotinic acid was filtered off and acetone (300 ml) and ether (600 ml) were added to the filtrate. Grey solid hydrobromide salt was collected, washed with ether, dried at the pump and recrystallised from ethanol (750 ml). The hydrobromide salt was collected as a lustrous grey solid (68 g).

The hydrobromide salt was dissolved in ethanol (600 ml) with warming and the solution was passed through a 4 ft × 1.5 inch column of Amberlite IR-45(OH) ion-exchange resin. Evaporation of solvent gave a yellow solid which was recrystallised from acetone:ethanol (×2) to give 1-octadecylpyridinium-4-carboxylate (I) as a pale yellow solid. The solid was dried in vacuo ($P_2O_5$) at 55°/1 mm for 5 h.

Yield: 31.5 g, 34%.

TLC: Silica plates, methanol, iodine $R_f$ 0.42 hydrobromide and betaine.

m.p.: 206°–208° (decomposition).

TLC/Iatroscan: Indicates single pure compound.

IR, NMR: Consistent with structure.

The compound (I) thus prepared was dissolved in filtered North Sea water at a temperature above its Krafft point (63° C.) to give a solution containing 2,000 ppm. This solution was tested for its oil displacement capability as follows: a glass capillary column of 1.3 mm internal diameter, 1 cm in length and sealed at one end was filled with Forties crude oil and immersed in the solution of surfactant containing 2,000 ppm. The time taken to displace all the crude oil was measured at different temperatures of the solution.

Compounds II, III, IV and V prepared in Examples 2 to 5 were tested in the same way.

Capillary oil displacement time

Compound (I): 5 seconds at 83° C.
Compound (II): was incompletely soluble at 90° C. to 2,000 ppm and released the oil from the capillary in 28 seconds at 90° C.
Compound (III): was incompletely soluble at 89° C. in sea water to 2,000 ppm and released the oil from the capillary in 10 seconds at 89° C.
Compound (IV): 4 seconds at 40° C., 2 seconds at 84° C.
Compound (V): 6 seconds at 35° C., 3 seconds at 50° C., 2 seconds at 85° C.

The dynamic interfacial tension was determined using the spinning drop method. Results as follows:

Compound (I): mNm$^{-1}$ against Forties Crude, 0.033 at 7 minutes at 70° C., 0.22 at equilibrium at 70° C.
Compound (II): —
Compound (III): —
Compound (IV): 0.15 at 8 minutes at 43° C., Krafft point 40° C. 0.29 at 23 minutes at 43° C. 1 at 80 minutes at 43° C.
Compound (V): very low at 60° C., Krafft point 54° C.

EXAMPLE 2

Preparation of 1-hexadecylpyridinium-3-sulphonate

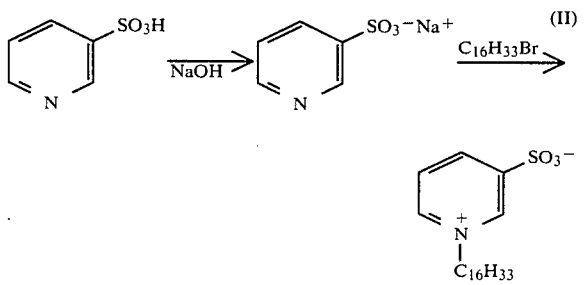

Pyridine-3-sulphonic acid was dissolved in hot water (31.8 g, 0.2M in 85 ml). Sodium hydroxide (8 g, 0.2M) in water (20 ml) was added slowly. A slight excess was necessary to bring the pH of the solution to 8. The solution was evaporated (using xylene) to give an off-white solid. The solid was collected, ground and dried (P$_2$O$_5$) in a vacuum oven for 5 h at 60°/0.2 mm.

The dry white solid (35 g, 0.19M) and hexadecyl bromide (86.9 g, 0.285M) were heated to 190°–200° C. for 0.5 h. The mixture was then digested with ethanol (300 ml), insoluble material filtered off from the cold solution and the solid residue was recrystallised from ethyl acetate-ethanol ($\times 2$). The off-white solid was dried in vacuo (P$_2$O$_5$) for 6 h at 50°/0.8 mm.
Yield: 35 g, 48%.
TLC: Single spot, R$_f$ 0.65 (methanol, H$_2$SO$_4$).

m.p.: Begins shrinking, 170°–250°, not completely melted.

NMR: $^1$H CDCl$_3$ Spectrum confirms structure, no impurity bands.

EXAMPLE 3

Preparation of 1-hexadecylpyridinium-4-ethanesulphonate

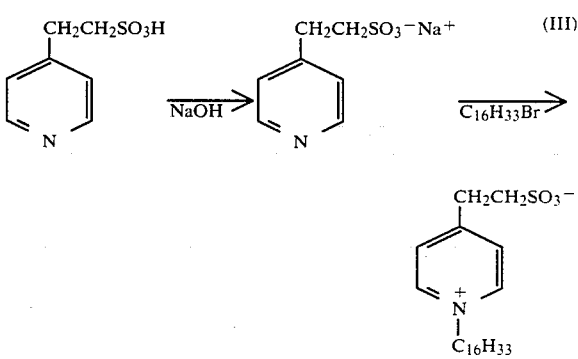

Pyridine-4-ethanesulphonic acid (56.1 g, 0.3M) was dissolved in water (70 ml) with warming. Sodium hydroxide (12 g, 0.3M) in water (40 ml) was added to the warmed solution to pH 8.5 and the solution was evaporated to give a white solid. This was dried at 80°/0.5 mm (P$_2$O$_5$) for 2 h. The white solid was heated above 100° in vacuo to remove final traces of water.

Pyridine-4-ethanesulphonic acid sodium salt (0.3M) and hexadecyl bromide (91.5 g, 0.3M) were heated to 190° for 0.5 h. The black solid was digested with boiling ethanol (2$\times$200 ml) and filtered. The off-white solid which crystallised from the filtrate was collected and was recrystallised from ethanol:ethyl acetate (1:1)$\times$2. The off-white solid was dried at 1 mm/50° for 4 h (P$_2$O$_5$).

IR: indicated ethanol present. Further 6 h drying. IR indicates some reduction in OH band.
Yield: 4.8 g, 4%.
MP: Softens 195°, decomposition begins 220°.
TLC: Product R$_f$ 0.50. Slight base-line and high R$_f$ impurities (Methanol, Iodine).

EXAMPLE 4

The compound of formula:

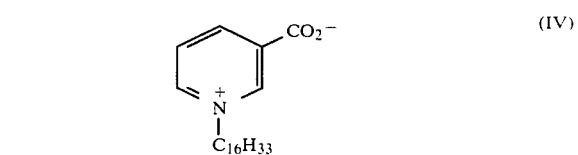

was prepared in a manner similar to that employed in Example 1 except that nicotinic acid and 1-bromohexadecane were used. The compound IV was tested as described above.

EXAMPLE 5

The compound of formula:

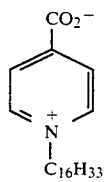 (V)

was prepared as described in Example 1 except that 1-bromohexadecane was employed.

The compound V was tested as described above.

EXAMPLE 6

Sand Column Test

A sand column containing 60 g of Forties separator sand was prepared as follows: the column was flooded with formation water and then with Forties crude oil. The column was then flooded with the same formation water until no further oil was displaced to get a condition representing post water flood residual oil satuation (SORW). A 2000 ppm solution of the betaine of Example 5 in Forties sea water at 70° C. was then employed to flood the column. Oil was displaced from the column. This demonstrates that the betaine solution will displace crude oil from the Forties formation material.

The betaines of the present invention have an advantage over other betaines in that they can be prepared in a one step chemical reaction from readily available moderately priced starting materials. Other betaines require a two stage preparation. Further the betaines of the present invention are characterised by low interfacial tensions (in solution against oil), high water solubility, high salinity tolerance, high divalent metal ion tolerance, temperature stability and improved wettability. In these respects they are superior to many known surfactants and the majority of previously published betaines.

I claim:

1. A method for recovering oil from a formation which method comprises the steps of injecting an aqueous medium containing a surfactant into the formation, displacing the oil from the formation and recovering the displaced oil, wherein the surfactant is a betaine of formula

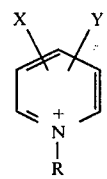

wherein

R is $C_8$ to $C_{24}$ alkyl which may optionally be substituted by inert substituents;

Y is H, $CO_2^-$ or a $SO_3^-$;

when Y is H, X is $CO_2^-$, $SO_3^-$ or $(CH_2)_m SO_3^-$ where m is 1 or 2;

when Y is $CO_2^-$, X is $CO_2^-$;

and when Y is $SO_3^-$, X is $SO_3^-$.

2. A method according to claim 1 wherein the aqueous medium is sea water or formation water with a total ionic content of up to 150,000 ppm of which up to 50,000 ppm may be divalent ions.

3. A method according to either of the preceding claims 1 or 2 wherein the concentration of the betaine in the aqueous medium is in the range 200 to 100,000 ppm.

* * * * *